US00RE47367E

(19) United States
(12) Reissued Patent
Green

(10) Patent Number: US RE47,367 E
(45) Date of Reissued Patent: Apr. 30, 2019

(54) SEXUAL STIMULATION DEVICE

(71) Applicant: Robert Madson Green, Vista, CA (US)

(72) Inventor: Robert Madson Green, Vista, CA (US)

(21) Appl. No.: 14/873,094

(22) Filed: Oct. 1, 2015

Related U.S. Patent Documents

Reissue of:
(64) Patent No.: 8,998,796
Issued: Apr. 7, 2015
Appl. No.: 13/785,922
Filed: Mar. 5, 2013

U.S. Applications:
(60) Provisional application No. 61/609,122, filed on Mar. 9, 2012.

(51) Int. Cl.

| | |
|---|---|
| ***A61F 5/00*** | (2006.01) |
| ***A61H 19/00*** | (2006.01) |
| ***A61N 1/18*** | (2006.01) |
| ***H01R 13/62*** | (2006.01) |
| ***A61F 5/41*** | (2006.01) |
| ***A61N 1/36*** | (2006.01) |
| *A61H 9/00* | (2006.01) |

(52) U.S. Cl.
CPC ..... *A61H 19/32* (2013.01); *A61F 5/41* (2013.01); *A61N 1/18* (2013.01); *A61N 1/36007* (2013.01); *A61N 1/36014* (2013.01); *H01R 13/6205* (2013.01); *A61F 2005/412* (2013.01); *A61F 2005/418* (2013.01); *A61H 9/0057* (2013.01); *A61H 2201/0176* (2013.01); *A61H 2201/10* (2013.01)

(58) Field of Classification Search
CPC ..... A61H 19/30; A61H 19/32; A61N 1/18; H01R 13/6205; H01R 13/22; H01R 11/30; H01R 30/06
USPC ..... 600/38–41; 439/38–40
See application file for complete search history.

(56) References Cited

U.S. PATENT DOCUMENTS

| | | | | |
|---|---|---|---|---|
| 3,820,533 | A | 6/1974 | Jones | |
| 4,378,008 | A | 3/1983 | Osbon | |
| 4,641,638 | A | 2/1987 | Perry | |
| 4,856,498 | A | 8/1989 | Osbon | |
| 4,856,499 | A | 8/1989 | Kelly | |
| 5,195,943 | A | 3/1993 | Chaney | |
| 5,234,401 | A | 8/1993 | Yamanaka | |
| 5,244,453 | A | 9/1993 | Osbon et al. | |
| 5,421,808 | A | 6/1995 | Osbon et al. | |
| 5,462,514 | A | 10/1995 | Harris | |
| 5,669,869 | A * | 9/1997 | Strom | A61F 5/41 600/38 |
| 5,707,341 | A | 1/1998 | Mathewuse | |

(Continued)

FOREIGN PATENT DOCUMENTS

WO WO 0158394 A1 * 8/2001 ..... A61F 6/04

*Primary Examiner* — Catherine S Williams
(74) *Attorney, Agent, or Firm* — Fish IP Law, LLP

(57) ABSTRACT

A sexual stimulation device is described. The device uses electrical stimulation and provides advantages in means to make gentle and safe electrical contact to the user's penis that is contained within a fluid environment. The device includes both a containment vessel as well as electrical connection embodiments that incorporate magnetically actuated contacts the can be quickly disconnected. The device provides flexibility for programmed and varied stimulation to different regions of the user's penis.

20 Claims, 7 Drawing Sheets

(56) References Cited

U.S. PATENT DOCUMENTS

| | | | | |
|---|---|---|---|---|
| D398,998 | S | 9/1998 | Gamper et al. | |
| 5,876,324 | A | 3/1999 | Trouchine | |
| 6,007,836 | A * | 12/1999 | Denzer | A61F 6/04 128/842 |
| 6,036,635 | A | 3/2000 | Altshuler | |
| 6,266,560 | B1 | 7/2001 | Zhang et al. | A61N 1/36007 604/20 |
| 7,566,299 | B2 | 7/2009 | Montgomery | |
| RE41,463 | E * | 7/2010 | Boutos | A61N 1/0408 600/38 |
| 2007/0093687 | A1* | 4/2007 | Hoefer | A61F 5/41 600/41 |
| 2010/0010292 | A1 | 1/2010 | Talbot et al. | |
| 2012/0002848 | A1 | 2/2012 | Bilbrey et al. | |
| 2012/0028480 | A1* | 2/2012 | Bilbrey et al. | 439/39 |
| 2015/0000095 | A1 | 1/2015 | Schultz | |
| 2015/0000952 | A1* | 1/2015 | Schultz | 174/78 |

* cited by examiner

SEXUAL STIMULATION DEVICE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application claims benefit of U.S. Provisional application 61/609122, entitled Sexual Stimulation Device, Filed on 9 Mar. 2012, by the same inventor.

STATEMENT REGARDING UNITED STATES FEDERALLY SPONSORED RESEARCH

There is no related federally sponsored research.

TECHNICAL FIELD

The present invention relates to a sexual stimulation device for use by males. The device is useful both for personal stimulation as well as a treatment for erectile dysfunction.

BACKGROUND OF THE INVENTION

The use of external devices to aid in a male obtaining an erection and further stimulation to the point of orgasm are known. However there is still a large demand and market for such aids especially in the treatment of erectile dysfunction. In recent years drugs for the treatment of erectile dysfunction have become a billion dollar industry in the United States alone. These drugs however can have side effects and unsafe interactions with other medications. The drugs directly affect the users blood pressure. Blurred vision, loss of vision, deleterious effects on hearing are known side effects. In some cases the user's reaction results in uncontrolled and uncomfortable erection that may result in permanent harm. Users who are on other medication for treatment of heart disease or control of blood pressure are advised against their use.

Previously known mechanical devices that encapsulate the penis are known. Examples of such devices are described in U.S. Pat. Nos. 5,234,401, 5,707,341, 6,266,560 and US patent application 201000010292. However once encapsulated in a device applying added stimulation is limited. The encapsulation device itself acts as a barrier to touching or stimulation of the penis.

Consequently, there is an ongoing need for innovation in this area. There is a need for a device that can provided stimulation and treatment of erectile dysfunction and further can add other stimulation effects without the side effects of medication. There is a need for a new mechanical device that can safely provide means for stimulation even after a user's penis is contained with in an encapsulating device.

DISCLOSURE OF THE INVENTION

The present invention addresses the aforementioned deficiencies in the prior art. A device is described that allows a user to encapsulate his penis in a stimulating fluid environment. The invented device provides a comfortable seal while maintaining a fluid environment and preventing leaks or loss of the fluid. In some embodiments the device also provides means for pneumatic or vacuum stimulation. Other embodiments of the device provide novel water tight electrical interconnects to provide means for electrical stimulation as well. The electrical contact are magnetically attached to provide for a safe connection means that will also break the connection should wires connecting to a electrical stimulation power source become entangled or tripped over. Further embodiments provide for electrical contact for electrical stimulation to the penis both through the fluid in the encapsulation device and through a direct electrical connection.

DETAILED DESCRIPTION

Figure 1:
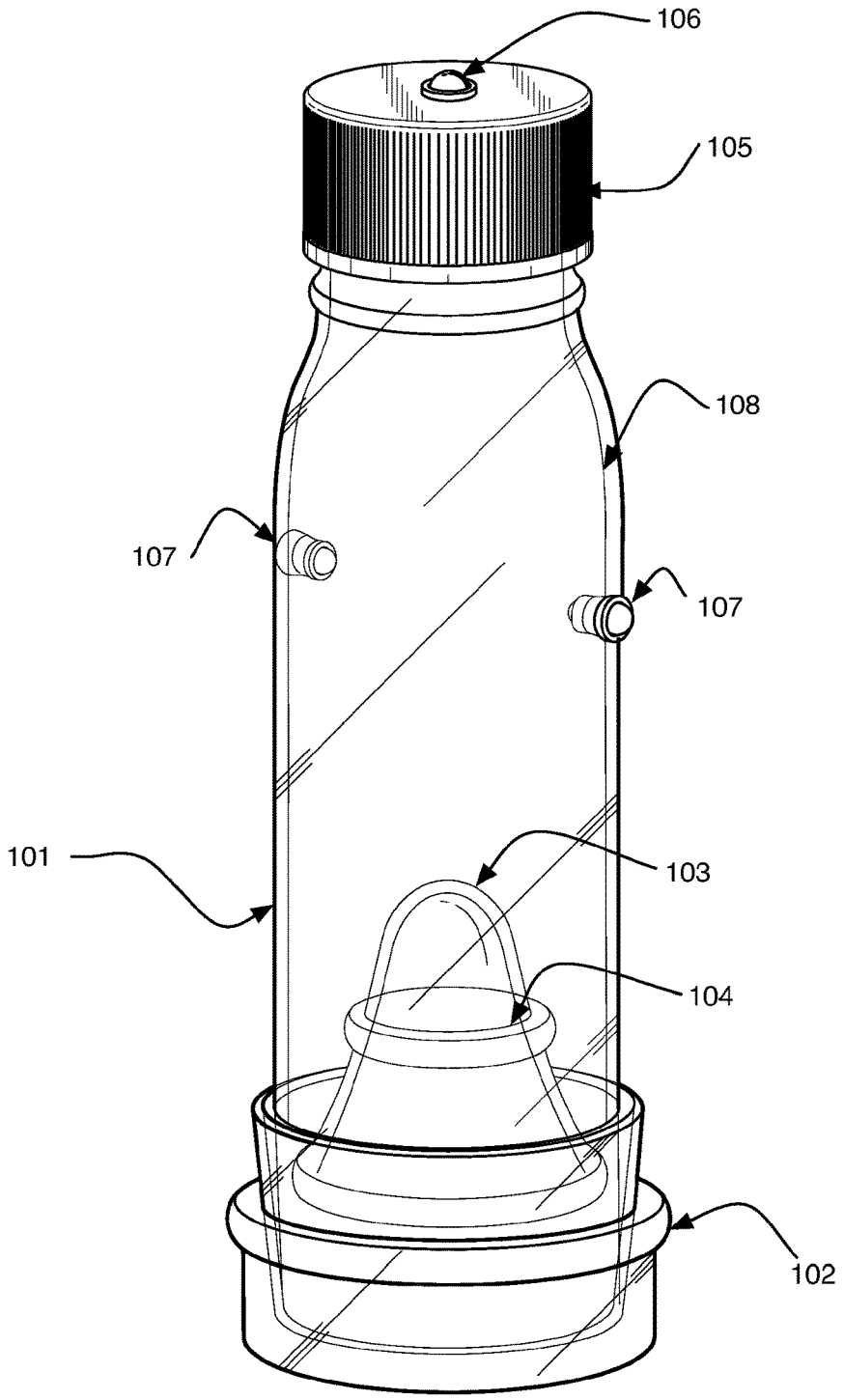
FIG. 1 is a perspective drawing of the invented device.

Referring to FIG. 1, the invented sexual stimulation device is seen to be comprised of a main body, cylindrical, bottle-like, structure 101 that includes a cap 105 and a flexible sealing structure 102 at the bottom through which a user's penis is inserted. The main body is open at the bottom, thus forming an open cylinder. The flexible sealing structure 102 is made of a pliable rubber-like material sized to attach to the cylinder of the main body. The fitting may be composed of any suitable flexible rubber-like material non-limiting examples include natural rubber, synthetic rubber and silicone. The main body may be constructed of any material typically used for bottles such as plastic or glass. Non-limiting examples of suitable plastic material includes polycarbonates, acrylics, and high-density polyethylene. The flexible sealing structure 102 further comprises a tapered structure including a compression ring 104 and a top portion 103. The ring 104 forms a watertight seal around the user's penis. The top conical section 103 is slit or perforated to allow the penis to penetrate through the fitting to the inside of the main body 101. The cap 105 is preferably a threaded screw cap but in other embodiments is also a friction-fitting cap and in another embodiment, not shown, is a cork or stopper. The invention further includes electrical connections 106, 107 that provide an electrical connection through the wall 108 of the main body or through the cap. In the embodiment shown there are three electrical connections that go through either the wall 108 or the cap 105. In other embodiments, not shown, there is a single electrical connection and in other embodiments, also not shown, there are a plurality of electrical connections that may pass through either the cap, the walls 108 or both. The details of the electrical connection are discussed in conjunction with FIG. 6.

Figure 2:
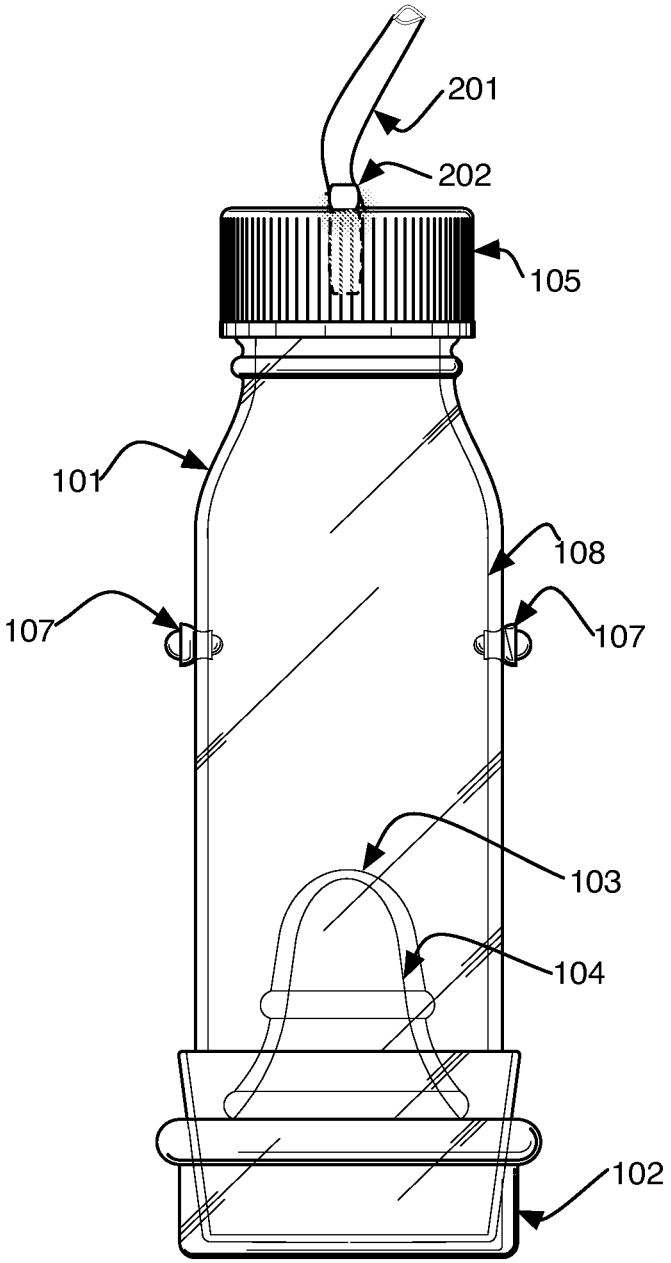
FIG. 2 is a side view of the invented device showing additional embodiments for a vacuum connection.

In another embodiment shown in FIG. 2 the cap further includes a fitting 202 for tubing 201. The fitting provides an air and watertight connection between the interior of the main body 101 and the exterior. The fitting 202 is typically a plastic tube that is sized to fit a hole through the top of the cap 105. In one embodiment the fitting 202 is welded into the cap. In another embodiment the fitting is glued in place. In use, a flexible tube 201 is attached to the fitting 202. The other end of the flexible tube may be attached to a vacuum pump or a vacuum may be applied by mouth. In either case a partial vacuum is thereby applied to the interior of the main cylinder body 101. Other features shown in FIG. 2 are included for reference and are discussed in conjunction with other Figures. The tubing connection may be instead of the electrical contact 106 in the top of the cap or in addition to the electrical connection 106. In other embodiments, not shown, the tubing connection can be made through the wall 108 of the main body 101.

Figure 3:
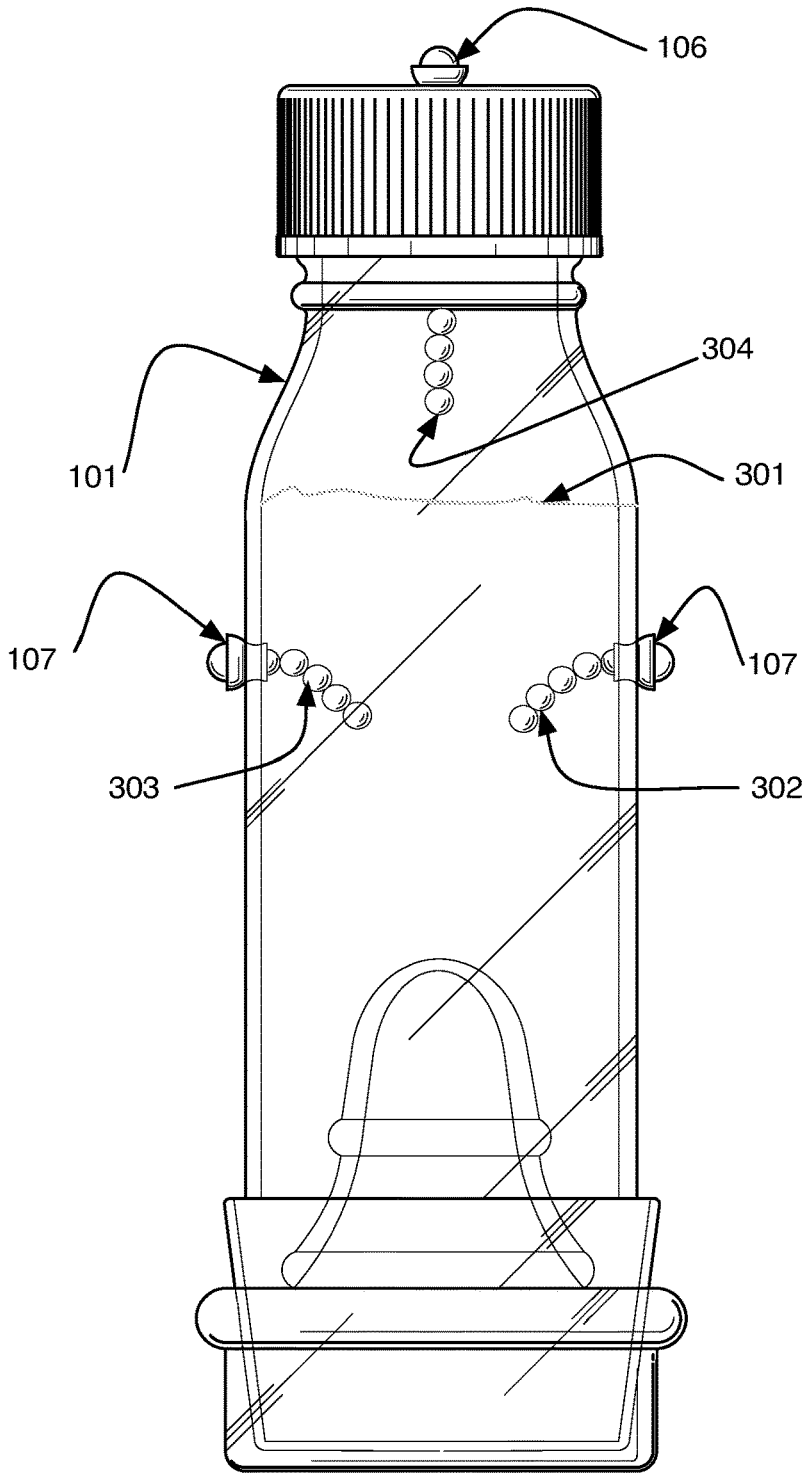
FIG. 3 is a side view of the invented device showing further electrical connection embodiments.

In another embodiment, shown in FIG. 3, electrical contact elements 302, 303, 304 are included in the interior of the main cylindrical body 101. The electrical contact to the outside is made through fittings 106, 107 that provide an airtight and watertight seal while still permitting an electrical contact. In the embodiment shown the electrical contacts 302, 303, 304 on the interior are comprised of a chain of linked metal spheres. In a preferred embodiment the metal spheres are magnets and are held together in the chains as shown by magnetic forces. In another embodiment the chain of spheres are held together physically by welding the spheres together. In another embodiment the spheres are held together physically with wire stitching not shown. In another embodiment, not shown, the electrical contacts in the interior are comprised of wires.

Also shown in FIG. 3 is the use of fluid to further the electrical contact. The interior of the main body is filled with fluid 301 to provide a better electrical contact and for safety purposes the contact is over a wider area of the user's penis. Point contacts can cause burns and permanent damage. The fluid 301 is typically water or a water solution of sodium chloride or sodium bicarbonate. Solution concentrations range from 1% to approximately 10%.

Figure 4:
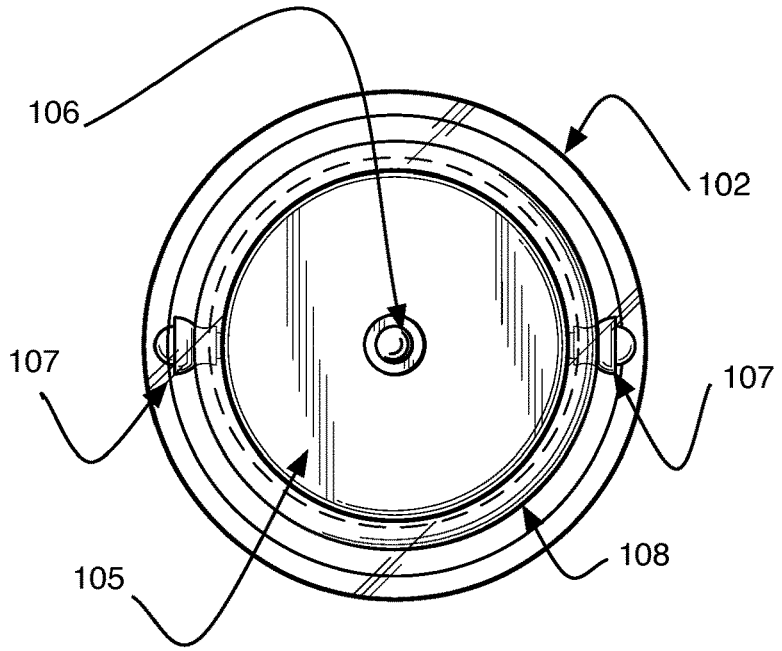
FIG. 4 is a top down view of the invented device.
Figure 5:
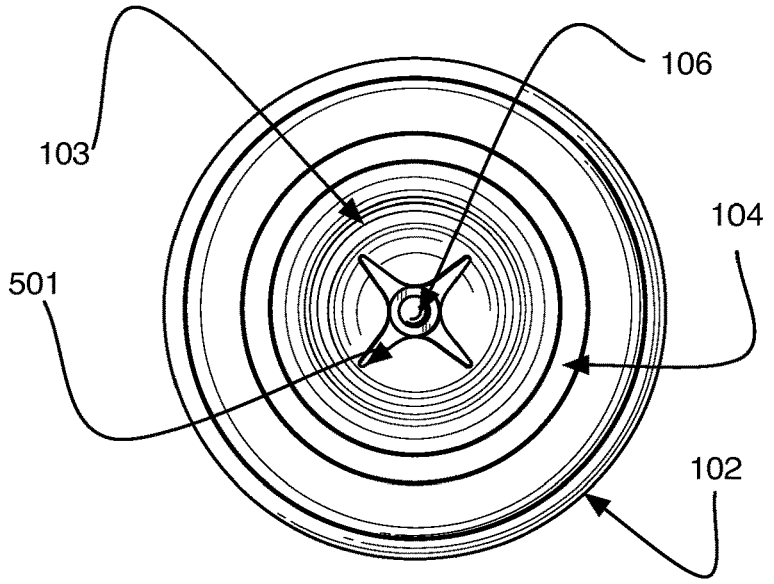
FIG. 5 is a bottom up view of the invented device.

Further clarity in the construction of the device is provided in the added views of FIGS. 4 and 5. FIG. 4 shows a top down view on the invented device where the electrical connector 106 is seen in the top of the cap 105. The electrical connectors 107 in the main body of the device are seen to provide electrical continuity through the wall 108. The flexible sealing structure 102 that provides a seal on the bottom of the main cylindrical body can also be seen as a tight fitting concentric cap to the main cylindrical body.

Referring now to FIG. 5, a bottom up view of the invented device is seen. The flexible sealing structure 102 is seen to cap the bottom of the cylindrical main body and the flexible fitting further includes a ring 104 in its conical interior 103 that provides a watertight seal around the user's penis. The top of the conical section 103 is seen to contain slits or an opening 501 that allows penetration of the penis into the interior of the main cylindrical body. The flexible sealing structure 102 and the conical section are composed of pliable material that will conform to the penis and provide a watertight seal around the penis when inserted through the opening 501. Also seen in FIG. 5 is the bottom of the electrical connector 106 that is located in the top cap of the device.

Figure 6:
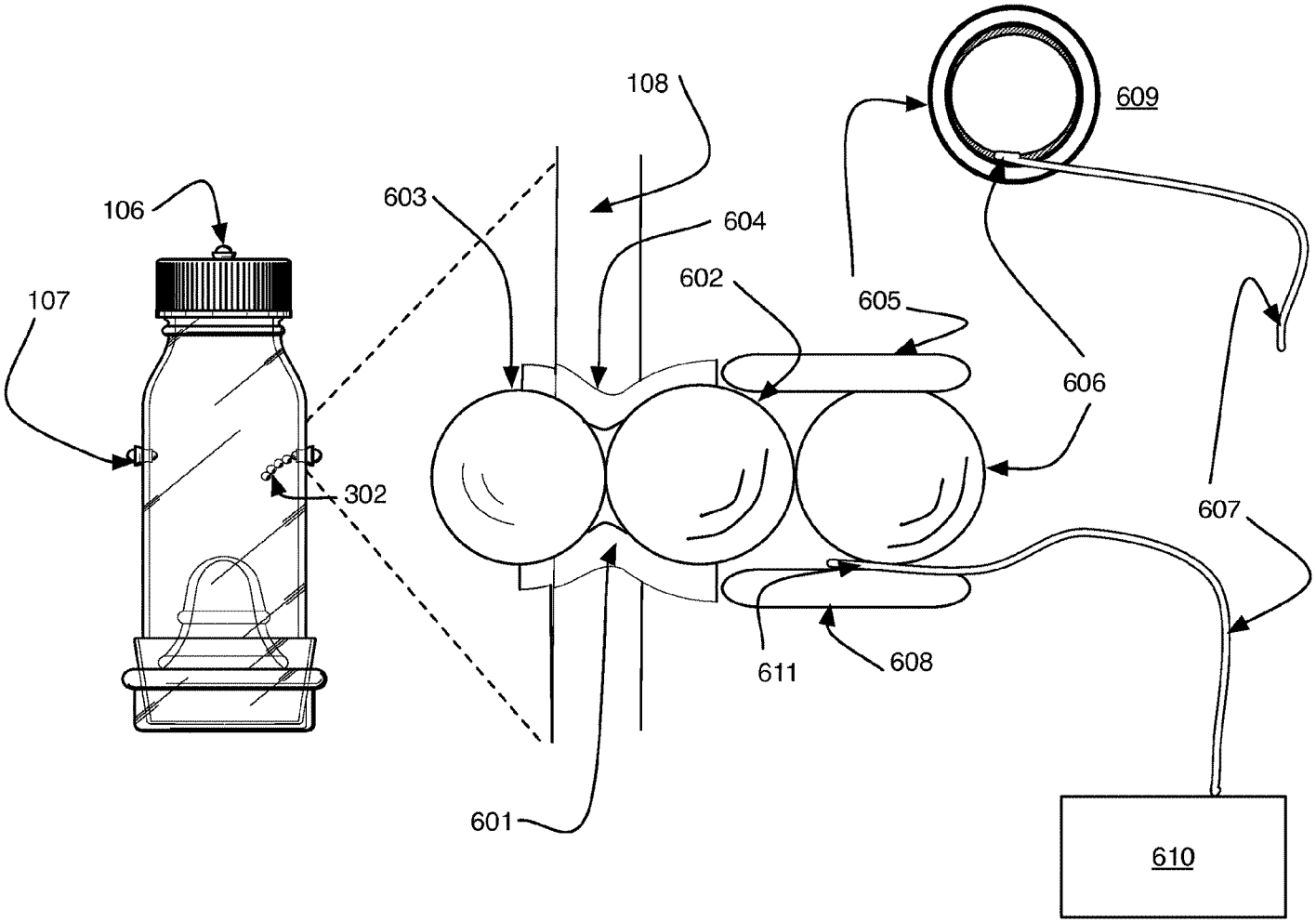
FIG. 6 shows an expanded view of the magnetic electrical connector embodiment.

Details of the electrical connectors 106, 107 embodiment are shown in FIG. 6. The connector assembly provides means to provide electrical connection between the interior of the cylindrical main body and the electrical contacts 302 contained therein and an exterior source for electrical stimulation 610. The source for electrical stimulation includes devices know for such use, nonlimiting examples include the stimulation device model ET-3 12B sold under the name ErosTek by ECForbes Inc. of San Rafael, Calif. USA and the electrical stimulation devices sold under the names Flexi Tens and Bodyclock DUO by tensunit.com [the model and company names ET-312B, ErosTek are trademarks of ECForbes, Inc. to the best of the author's knowledge used, but not federally registered and the names Flexi Tens and Bodyclock DUO are similarly trademarks used by a company identifying itself as tensunit.com again to the best of the author's knowledge used but not registered trademarks]. Contacts with the power source may be made exclusively through the contacts 106, 107 on the device or there may be additional contacts to the user's body. A non-limiting example would be where one pole of the power source is attached to the users scrotum and the other pole is attached to the contacts 106, 107 on the device.

In another embodiment multiple power sources or power sources with multiple channels may be used such that the power and frequency of the electrical stimulation through each separate contact 106, 107 is different. Such variation is used to provide a programmed stimulation where the location, frequency and intensity of the stimulation are varied with time.

The device is shown with three contacts points. In other embodiments there may be fewer contact points. In one embodiment there is a single electrical contact point. In another embodiment there are two, three or more contact points.

The electrical connection is provided by an electrical connector 106, 107 that provides an airtight and watertight seal across the walls 108 of the invented device. The connector 107 is comprised of two metallic spheres 602, 603 that are tightly fit in the interior of a short length of flexible tubing 601. Nonlimiting example of material for the flexible tubing include natural and synthetic latex, polyvinyl chloride and silicone. The tubing and the spheres are sized to tightly fit a hole 604 through the wall 108 of the device. In another embodiment the tubing is glued in place to provide a more secure seal. The metallic spheres 602, 603 contact each other and provide electrical connectivity through the wall boundary. In a preferred embodiment the metallic spheres are magnetic and are held together through magnetic forces. In another embodiment the metallic spheres are welded together and in another embodiment, not shown, there is a wire strung through the spheres to ensure electrical connectivity. The connection to the contact 302 on the interior of the device has already been described. The exterior contact 608 is comprised of at least one sphere 606 contained within the interior of a short length of flexible tubing 605. The sphere and the tubing selected to provide a tight fit such that the sphere will not fall from the tubing. The exterior contact 608 further includes a wire connector 607 that makes electrical contact 611 with the metallic sphere 606. A cross sectional view of the external contact is also shown 609. The metallic sphere is magnetic and makes electrical contact to the sphere 602 through magnetic attraction and contact to the sphere 602. A connection is thereby completed from the external stimulation power source 610 through the wire 607 and the contact 611 through spheres 606, 602, 603 to the interior contact 302. The contact between the exterior contact 608 and the sphere 602 is maintained by magnetic forces such that if the wire 607 is pulled the contact can be broken. The size of the magnetic spheres 606, 602, 603 and the permanent magnetic forces therein are selected such that the pulling on the wire 607 will break the connection before physical harm to the user occurs. The magnetic connection thus described also provides the user with an emergency disconnect should the electrical power from the source 610 becomes too high or is perceived as too intense or the device 610 malfunctions.

Figure 7:
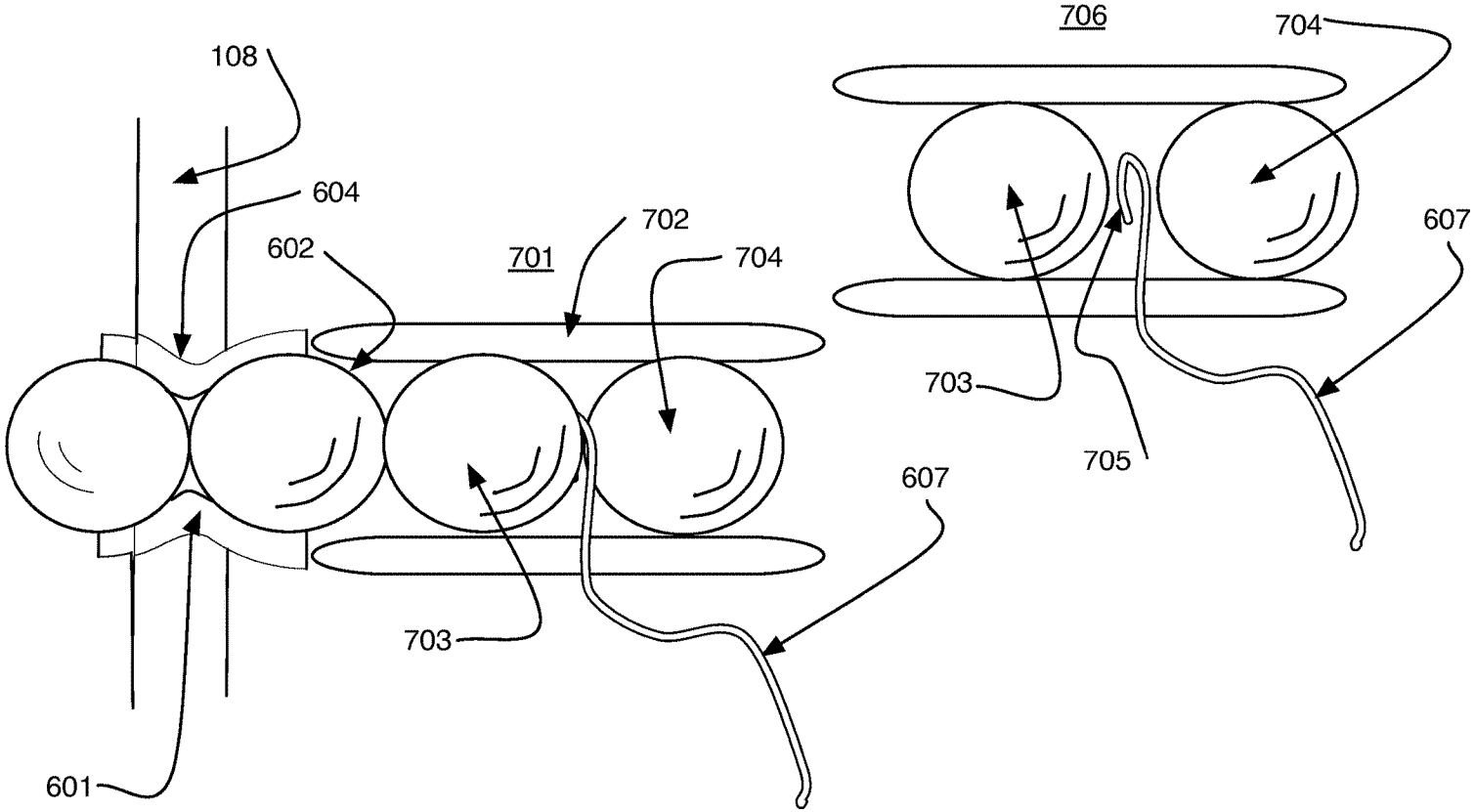
FIG. 7 shows another embodiment of the magnetic electrical connector.

A second embodiment of the external contact is shown in FIG. 7. The external contact 701 is comprised of two metallic magnetic spheres 703, 704 located as before in a length of flexible tubing 702. A wire 607 passes through the wall of the tubing 702 and the end of the wire is formed into a loop 705 positioned between the two magnetic spheres. The second view 706 shows the spheres separated to better see the loop 705. The spheres are attracted and make physical contact to the wire loop to create an electrical contact. The sphere 703 makes contact to the sphere 602 to create the electrical connection through the connector 604 positioned in the wall 108.

All embodiments of the electrical connector in the wall of the device and the interior and exterior electrical contacts are, as shown, applicable to the present invented device but could be used in any application where a sealed electrical connection through a wall is required. In another embodiment not shown the interior electrical contact is replaced with an electrical contact that is the same as the exterior electrical contact.

For clarity the nomenclature used herein for the connectors and contacts is repeated. The embodiment 604 that provides electrical continuity across the wall of the device is called a connector. The embodiments 302, 303, 304, 608, 701 that make electrical contact to the connector 604 are termed contacts. There are three embodiments described for the contacts: an interior contact 302, 303, 304 and two exterior embodiments 608, 701.

Figure 8:
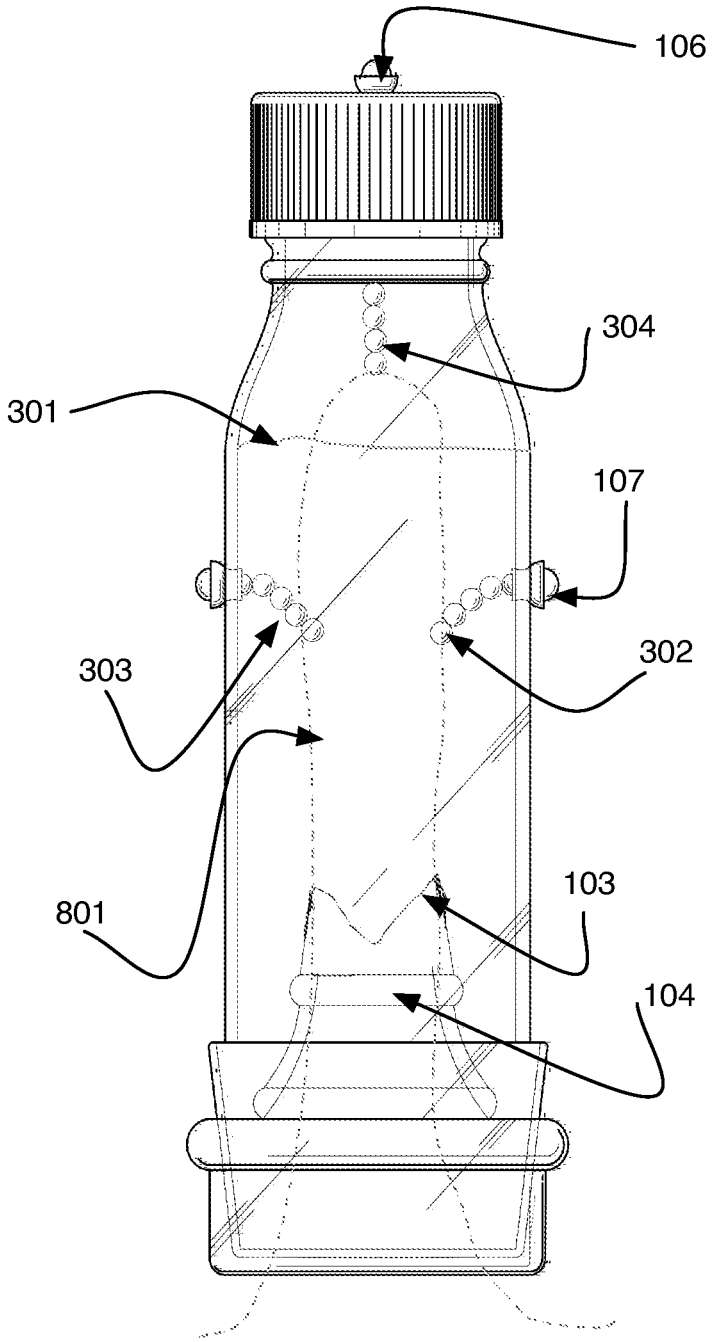
FIG. 8 shows embodiments of the invention as they would appear during use.

Referring now to FIG. 8, embodiments of the device are shown as they would appear in use. The user inserts his penis 801 through the opening 103 in the bottom of the device the flexible ring 104 and the walls of the opening 103 forming a air and water tight seal with users penis 801. The device is at least partially filled with fluid 301 and the interior contacts 302, 303, 304 gently contact the user's penis 801. It is noted that the contacts 302 and 303 are submerged and the contact 304 is not. In one embodiment the power, frequency and intensity of the submerged contacts 302, 303 is different from that applied to the non-submerged contact 304. The connections to the power sources are not shown but were discussed earlier.

A sexual stimulation device is described. The device uses electrical stimulation and provides advantages in means to make gentle and safe electrical contact to the user's penis that is contained within a fluid environment. The device includes both a containment vessel as well as electrical connection embodiments that incorporate magnetically actuated contacts the can be quickly disconnected. The device provides flexibility for programmed and varied stimulation to different regions of the user's penis.

What is claimed is:

1. A sexual stimulation device, said sexual stimulation device comprising:

a. a [cylindrical] main body having a [top and a] bottom[, b. a cap removably attached to the top of the main body, c. a flexible sealing structure attached to the bottom of the main body wherein the flexible sealing structure is comprised of an external cap structure sized to fit and seal with the bottom of the main body and a central conical structure] that is perforated and sized to *form a watertight* seal [with] *around a fluid environment containing* a user's penis[, d] *b*. [at least one] *a first* electrical connector that is fit through a wall of the main body [wherein the electrical connector is comprised of two magnetic spheres fit in the interior of a flexible tube said flexible tube is sized to form a seal when inserted in a hole in the wall of the main body,]*;*

[e] *c*. [at least one] *a first* interior electrical contact that attaches to the electrical connector [and], is located in the interior of the main body, and, during use, makes an electrical connection to the user's penis[,] *through the fluid environment; and*

[f] *d*. [at least one] *a first* exterior electrical contact [that] attached to the electrical connector and [is] located exterior of the main body,

[g. wherein the at least one exterior electrical contact is comprised of at least one magnetic sphere, said magnetic sphere in electrical contact with a wire and a magnetic attractive force between the magnetic sphere of the exterior electrical contact and the electrical connector causes the spheres to maintain physical contact and thereby provide electrical continuity between the at least one interior electrical contact, through the electrical connector and to the at least one exterior electrical contact, and, h] wherein the *first* exterior electrical contact is further attached [through a wire connection to an] *to a first* electrical power source, *and wherein* said *first* electrical power source [providing] *provides* electrical stimulation to the user's penis *via the first exterior electrical contact, the first electrical connector, the first interior electrical contact, and the fluid environment, respectively*.

[2. The device of claim 1 further comprising an electrical connector located in the cap and wherein the electrical connector in the cap is comprised of two magnetic spheres fit in the interior of a flexible tube said flexible tube is sized to form a seal when inserted in a hole in the wall of the main body.]

[3. The device of claim 1 further comprising a connector for tubing said connector for tubing passing through the cap and forming an air and water tight seal to the cap such that a length of tubing may be attached to the connector for tubing to allow a user to apply a partial vacuum to the interior of the cylindrical main body.]

4. The device of claim 1 wherein the main body [is made of] *comprises* plastic.

5. The device of claim 1 wherein the main body [is made of] *comprises* glass.

6. The device of claim 1 wherein the *first* exterior electrical connector is comprised of two magnetic [spheres] *metals*, said magnetic [spheres] *metals* making electrical contact to a wire *connected to the first electrical power source, and* said wire [having a loop in the end of the wire said loop] positioned between the [spheres] *metals*.

7. The device of claim 1 comprising:

a. [at least two] *a second* electrical [connectors] *connector* that [are] *is* fit through a wall of the main body [wherein each electrical connector is comprised of two magnetic spheres fit in the interior of a flexible tube said flexible tube is sized to form a seal when inserted in a hole in the wall of the main body,]*;* b. [at least two] *a second* interior electrical [contacts] *contact* that [attach] *attaches* to the [at least two] *second* electrical [connectors and are] *connector, and is* located in the interior of the main body and, during use, makes an electrical connection to the user's penis[,] *through the fluid environment; and* c. [at least two] *a second* exterior electrical [contacts] *contact* that [are] *is* attached to the [at least two] *second* electrical [connectors] *connector* and [are] *is* located exterior [of] *to* the main body,

[d. wherein the at least two interior electrical contacts and the at least two exterior electrical contact are comprised of magnetic spheres and a magnetic attractive force between the spheres and the electrical connector causes the spheres to maintain physical contact and thereby provide electrical continuity between the at least two interior electrical contacts and the at least two exterior electrical contact, and, e.] wherein the [at least two] *second* exterior electrical [contacts are] *contact is* further attached to [an] *at least one of the first* electrical power source [said electrical power source providing] *and a second electrical power source which provides* electrical stimulation to the user's penis *via the second exterior electrical contact, the second electrical connector, the second interior electrical contact, and the fluid environment, respectively*.

8. The device of claim 7 wherein the [at least two exterior electrical contacts are attached to two, separate,] *first and second* electrical power sources *provide at least one of a different power and frequency of electrical stimulation*.

9. An electrical connector for traversing a wall of a plastic or glass device, said connector comprising:

a. [two] *a first* magnetic [spheres] *metal and a second magnetic metal* fit in [the] *an* interior of a flexible tube, *wherein* said flexible tube is sized to form a seal when inserted in a hole in the wall of the device, b. at least one interior electrical contact *comprising a third magnetic metal* that attaches to the [electrical connector] *first magnetic metal through magnetic attractive force* and is located in the interior of the device [and makes an electrical connection], c. at least one exterior electrical contact *comprising a fourth magnetic metal* that [attached to the electrical connector] *attaches to the second magnetic metal through magnetic attractive force* and is located exterior of the device, d. wherein [the at least one interior electrical contact and the at least one exterior electrical contact are comprised of magnetic spheres and a magnetic attractive force between the spheres and the electrical connector causes the spheres to maintain physical contact and] *an electrical path through the fourth magnetic metal, the second magnetic metal, the first magnetic metal, and the third magnetic metal* thereby provide electrical continuity between the at least one interior electrical contact and the at least one exterior electrical contact.

*10. The device of claim 1, wherein the first electrical connector further comprises a first magnetic metal, wherein the first exterior electrical contact comprises a second magnetic metal, and wherein a magnetic attractive force between the first magnetic metal and the second magnetic metal provides electrical continuity between the first interior electrical contact and the first exterior electrical contact.*

*11. The device of claim 10, wherein the first magnetic metal is within an interior of a flexible tube fit through the wall of the main body.*

*12. The device of claim 11, wherein the flexible tube forms a watertight seal when inserted into a hole in the wall of the main body.*

*13. The device of claim 12, wherein the first electrical connector further comprises a second magnetic metal within the interior of the flexible tube.*

*14. The device of claim 13, wherein the first magnetic metal and the second magnetic metal are spheres.*

*15. The device of claim 14, wherein the main body is cylindrical.*

*16. The device of claim 10, wherein the magnetic attractive force between the first magnetic metal and the second magnetic metal causes the first magnetic metal and the second magnetic metal to maintain physical contact.*

*17. The device of claim 1, further comprising a cap removably attached to a top of the main body.*

*18. The device of claim 17, further comprising:*

*a. a second electrical connector that is fit through a wall of the cap;*

*a second interior electrical contact that attaches to the second electrical connector, and is located in the interior of the main body, and, during use, makes an electrical connection to the user's penis through the fluid environment; and*

*a second exterior electrical contact that is attached to the second electrical connector and is located exterior to the main body, wherein the second exterior electrical contact is further attached to at least one of the first electrical power source and a second electrical power source, which provides electrical stimulation to the user's penis via the second exterior electrical contact, the second electrical connector, the second interior electrical contact, and the fluid environment, respectively.*

*19. The device of claim 17, further comprising a connector for tubing that is fit through a wall of the cap to form an air and water tight seal to the cap such that a length of tubing may be attached to the connector for tubing to allow a user to apply a partial vacuum to the interior of the cylindrical main body.*

*20. The device of claim 1, further comprising a flexible sealing structure attached to the bottom of the main body, wherein the flexible sealing structure comprises an external cap structure that seals with the bottom of the main body.*

*21. The device of claim 20, wherein the bottom of the main body has a central conical structure that is perforated and seals with the external cap structure.*

*22. The device of claim 1, wherein the first exterior electrical contact is connected to the first electrical power source via a wire.*

* * * * *